United States Patent
Horii et al.

(10) Patent No.: US 12,203,931 B2
(45) Date of Patent: Jan. 21, 2025

(54) ORGANIC COLORED MICROPARTICLES, DIAGNOSTIC REAGENT KIT, AND IN VITRO DIAGNOSIS METHOD

(71) Applicant: Asahi Kasei Kabushiki Kaisha, Tokyo (JP)

(72) Inventors: Atsushi Horii, Tokyo (JP); Yoshiyuki Shiomi, Tokyo (JP); Nobuyuki Mimura, Tokyo (JP); Ken Muraoka, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 711 days.

(21) Appl. No.: 16/644,306

(22) PCT Filed: Sep. 18, 2018

(86) PCT No.: PCT/JP2018/034499
§ 371 (c)(1),
(2) Date: Mar. 4, 2020

(87) PCT Pub. No.: WO2019/059182
PCT Pub. Date: Mar. 28, 2019

(65) Prior Publication Data
US 2021/0080455 A1 Mar. 18, 2021

(30) Foreign Application Priority Data
Sep. 25, 2017 (JP) ................. 2017-183472

(51) Int. Cl.
*G01N 33/543* (2006.01)
*G01N 33/548* (2006.01)

(52) U.S. Cl.
CPC . *G01N 33/54388* (2021.08); *G01N 33/54313* (2013.01); *G01N 33/548* (2013.01)

(58) Field of Classification Search
None
See application file for complete search history.

(56) References Cited

U.S. PATENT DOCUMENTS

| | | | |
|---|---|---|---|
| 2010/0087552 A1 | 4/2010 | Shiomi et al. | |
| 2011/0020848 A1* | 1/2011 | Akamatsu | C07K 16/1275 435/7.92 |
| 2012/0225496 A1 | 9/2012 | Yoshida | |
| 2013/0338041 A1 | 12/2013 | Hamasaki et al. | |
| 2015/0293082 A1 | 10/2015 | Shiomi et al. | |
| 2016/0123974 A1* | 5/2016 | Horii | G01N 33/54386 422/420 |
| 2018/0011086 A1 | 1/2018 | Isoda et al. | |

FOREIGN PATENT DOCUMENTS

| | | |
|---|---|---|
| CN | 101595168 A | 12/2009 |
| EP | 3608670 A1 | 2/2020 |
| JP | H05-087812 A | 4/1993 |
| JP | H06-254373 A | 9/1994 |
| JP | 2004-184295 A | 7/2004 |
| JP | 2009-120901 A | 6/2009 |
| JP | 2009-133739 A | 6/2009 |
| JP | 4514233 B | 7/2010 |
| JP | 2011-220705 A | 11/2011 |
| JP | 2014-163758 A | 9/2014 |
| JP | 2015-001398 A | 1/2015 |
| JP | 2015-083696 A | 4/2015 |
| JP | 2017-138271 A | 8/2017 |
| WO | 2011/062157 A1 | 5/2011 |
| WO | 2012/124377 A1 | 9/2012 |
| WO | 2016/117054 A1 | 7/2016 |
| WO | 2018/186267 A1 | 10/2018 |

OTHER PUBLICATIONS

Achilonu et al., Dye-Protein Interactions: Protein staining and Dye-IgY, Dye-Dextran-IgY complexes for antigen detection, School of Molecular and Cellular Biosciences, University of KwaZua-Natal Pietermaritzburg, Jan. 2004, pp. 1-207. (Year: 2004).*
International Search Report issued in corresponding International Patent Application No. PCT/JP2018/034499 dated Dec. 25, 2018.
International Preliminary Report on Patentability and Written Opinion issued in corresponding International Patent Application No. PCT/JP2018/034499 dated Mar. 31, 2020.
Fang et al., "Application Research of Magnetic Cellulose Microspheres in The Detection of Pathogenic Microorganisms," Ion Exchange and Adsorption, 26 (5): 431-438 (Oct. 20, 2010) (see English abstract).
Ugelstad et al., "Monodisperse polymer particles—a step forward for chromatography," Nature, 303: 95-98 (May 5, 1983).

* cited by examiner

*Primary Examiner* — Gary Counts
(74) *Attorney, Agent, or Firm* — Morgan, Lewis & Bockius LLP

(57) ABSTRACT

The present invention provides organic colored microparticles used in an immunochromatography diagnostic kit, the microparticles having good background and test result reproducibility and sufficient detection sensitivity. These organic colored microparticles are characterized in that the average particle diameter is 100 to 650 nm; coloration intensity is 1.0 to 10.0; when a total of 100,000 particles are detected within a particle diameter range of 400 to 12000 nm, the percentage of coarse particles having a particle diameter of 700 nm or greater is 5% or less; and the sphericity represented by the major axis (L)/minor axis (D) is 1.0 to 2.5.

11 Claims, 2 Drawing Sheets

ORGANIC COLORED MICROPARTICLES, DIAGNOSTIC REAGENT KIT, AND IN VITRO DIAGNOSIS METHOD

FIELD

The present invention relates to organic colored microparticles derived from an organic polymer, and a diagnostic reagent kit and in vitro diagnosis method using the same.

BACKGROUND

Simple test reagents, diagnostic reagents and diagnostic kits have been developed in recent years that enable various tests to be carried out in a short period of time, such as tests for the presence or absence of bacterial and other pathogen infections, pregnancy tests, cancer marker tests or tests for the presence or absence of specific raw materials or harmful substances such as residual agricultural chemicals present in food. These products use a specific reaction between each test target substance and a substance that specifically reacts with the test target substance. In particular, numerous immunoassay methods using an antigen-antibody reaction between antigen and antibody have been developed, such as immunochromatographic assays, nephelometric immunoassays, enzyme immunoassays, chemiluminescence assays, radioimmunoassays or assays using surface plasmon resonance. These assay methods are used to test for illnesses at hospitals and clinics or test foods at food manufacturers. Among these, immunochromatographic assays offer a simple procedure and are inexpensive without requiring special equipment, instruments or knowledge, and are used to perform an extremely large number of tests based on their characteristic of enabling rapid diagnosis. In recent years, pregnancy test drugs have come to be sold at ordinary pharmacies and enable assays to be performed by ordinary consumers, and not only qualitative tests for testing for the presence or absence of a test target substance, but also quantitative tests for measuring the amount of a test target substance can also be performed.

A method referred to as the sandwich method and a method referred to as the competitive method is used for the measurement principle of immunochromatographic assays. The measurement type consists of a flow through type and a lateral flow type. Although various substances can be detected as test target substances during a test, a typical example thereof is an assay for detecting antigen according to the sandwich method, and is sequentially carried out using the procedure indicated below. However, the procedure is not limited to that indicated below.

(1) Antibody that specifically binds to an antigen serving as the test target substance is immobilized at a prescribed site of a chromatographic medium such as a nitrocellulose membrane to form a reactive site referred to as a test line (also referred to as "TL") at an arbitrary location on the chromatographic medium.

(2) A detection reagent is prepared in which a ligand (such as antibody) that specifically binds with the test target substance is loaded onto a labeling substance such as an enzyme, coloring particles, fluorescent coloring particles or magnetic particles, the detection reagent is coated onto a conjugate pad and dried to form a portion containing the detection reagent, which is combined with the aforementioned chromatographic medium to form an immunochromatographic diagnostic kit. A ligand refers to that which specifically binds with a test target substance, and examples thereof include antibodies and antigens, organic molecules and proteins.

(3) A specimen per se containing an antigen or a solution obtained by diluting the specimen with an arbitrary liquid is dropped onto, for example, a sample pad at a prescribed location of the aforementioned immunochromatographic diagnostic kit and the antigen and detection reagent are allowed to develop on the chromatographic medium.

As a result of this procedure, a labeling substance is captured through the antigen by the antibody immobilized on the chromatographic medium at the reactive site, and diagnosis is carried out by the immunochromatographic diagnostic kit by detecting the signal of the labeling substance. Although typical diagnoses consisted of qualitative diagnoses that only detected the presence or absence of antigen, more recently, quantitative diagnoses can also be carried out by detecting the intensity of that signal either visually or mechanically.

The methods used to load antibody onto a labeling substance can be broadly divided into two methods. The first method involves loading antibody by chemical bonding while the other method consists of loading by physically adsorbing onto the surface of the labeling substance. The method involving loading by chemical bonding is known to make it possible to effectively orient the antibody. However, it is generally thought that, since chemical bonding may be difficult depending on the antibody and in consideration of the simplicity of the handling procedure, there is a greater demand for methods involving particles capable of physically adsorbing antibody in order to accommodate a wide range of test targets. Among these, the following PTL1 reports the use of gold colloids while PTL2 reports the use of colored latex as particles capable of physically adsorbing antibody.

One of the requirements sought after in immunochromatographic assays is improved analytical sensitivity. This refers to being able to detect smaller amounts of test target substances. Since rapid diagnoses can be made by improving analytical sensitivity, analytical sensitivity is an important factor. The inventors of the present invention reported in the following PTL3 that analytical sensitivity can be improved by using deeply colored cellulose particles having a large particle diameter as coloring particles capable of physically adsorbing antibody.

On the other hand, another requirement of immunochromatographic assays is improving the background of the nitrocellulose membrane following immunochromatographic development. Here, "background" refers to the phenomenon that occurs in which the nitrocellulose membrane ends up being colored as a result of coloring particles becoming clogged in pores of the nitrocellulose membrane or undergoing non-specific adsorption. A poor background results in poor contrast between the nitrocellulose membrane and TL or causes the colored TL to be difficult to see, thereby making it difficult to determine the result in the clinical setting. A poor background can also make it difficult to recognize a negative TL (namely, lack of coloring). These phenomena have the potential to cause misdiagnoses. PTL3 does not mention whatsoever such problems associated with background.

CITATION LIST

Patent Literature

PTL1: Japanese Patent No. 4514233
PTL2: Japanese Unexamined Patent Publication No. 2004-184295
PTL3: International Publication No. WO 2011/062157

SUMMARY

Technical Problem

In consideration of the prior art, an object to be solved by the present invention is to provide organic colored microparticles for an immunochromatographic diagnostic kit that has favorable background and test result reproducibility and has adequate detection sensitivity.

Solution to Problem

As a result of conducting extensive studies and experiments to solve the aforementioned problems, the inventors of the present invention unexpectedly found that organic colored microparticles, for which the sphericity of the organic colored microparticles and the amount of coarse particles having a particle diameter of 700 nm or more are precisely controlled, can be developed without clogging the nitrocellulose membrane serving as the chromatographic medium, and as a result thereof, an immunochromatographic assay using these organic colored microparticles as colored particles demonstrates high detection sensitivity and superior test result reproducibility, thereby leading to completion of the present invention.

Namely, the present invention is as indicated below.

[1] Organic colored microparticles in which the average particle diameter is 100-650 nm, coloring intensity is 1.0-10.0, and when a total of 100,000 particles are detected over a range of particle diameter of 400 nm to 12000 nm, the prevalence of coarse particles having a particle diameter of 700 nm or more is 5% or less, and sphericity as represented by major axis (L)/minor axis (D) is 1.0-2.5.

[2] The organic colored microparticles described in [1] above, wherein the 10-90 wt % of the weight of the organic colored microparticles constitutes a coloring component.

[3] The organic colored microparticles described in [2] above, wherein the coloring component is a reactive dye.

[4] The organic colored microparticles described in [3] above, wherein the reactive dye has a pyrimidine structure or triazine structure.

[5] The organic colored microparticles described in any of [1] to [4] above, wherein hydrophilicity of the organic colored microparticles is 1.0-30.0.

[6] The organic colored microparticles described in any of [1] to [5] above, wherein a ligand is bound by physical adsorption.

[7] The organic colored microparticles described in [6] above, wherein the ligand is coated with casein.

[8] A diagnostic reagent kit containing the organic colored microparticles described in any of [1] to [7] above.

[9] The diagnostic reagent kit described in [8] above, which is an immunochromatographic kit.

[10] An in vitro diagnosis method containing a step for using the organic colored microparticles described in any of [1] to [7] above.

[11] The in vitro diagnosis method described in [10] above, which is an immunochromatographic method.

Advantageous Effects of Invention

Immunochromatography using the organic colored microparticles of the present invention as coloring particles demonstrates favorable background and test result reproducibility and has adequate detection sensitivity.

The present invention was found to demonstrate favorable background and superior test result reproducibility while maintaining high detection sensitivity by precisely controlling the sphericity of the organic colored microparticles and coarse particles having a particle diameter of 700 nm or more, thereby leading to the completion thereof.

PTL3 discloses that detection sensitivity is improved by using deeply colored organic colored microparticles having a large particle diameter as coloring particles of immunochromatography. However, since these microparticles have low sphericity and the spherical shape thereof is distorted, the microparticles end up getting caught in the pores of the nitrocellulose membrane when developed thereon, thereby resulting in the risk of leading to poor background.

On the other hand, the inventors of the present invention found that coarse particles having a particle diameter of 700 nm or more are the main cause of poor background when developing as coloring particles for immunochromatography and designated particles having a particle diameter of 700 nm or more as coarse particles. In PTL3, there is no mention whatsoever of coarse particles of 700 nm or more, and background ends up worsening if only the parameters indicated in this literature (such as CV value) are managed. Although methods for improving background include addition of an additive such as a surfactant or amino acids to the developing liquid, these methods have the risk of also causing a decrease in sensitivity.

The inventors of the present invention thought that if it were possible to make the shape of the particles approach that of a sphere and reduce the number of coarse particles that easily clog the nitrocellulose membrane, the particles would be developed without coloring the nitrocellulose membrane, or in other words, improve background. As a result of conducting experiments on the basis of this hypothesis, it was found that by precisely controlling the degree of polymerization, particles dyed using a reactive dye having a pyrimidine structure or triazine structure have a shape that approaches that of a sphere while also making it possible to reduce the number of coarse particles having a particle diameter of 700 nm or more. As a result of obtaining a favorable background while continuing to maintain high detection sensitivity by using such organic colored microparticles as coloring particles for immunochromatography, contrast with the TL becomes favorable, the presence or absence of color becomes easier to determine and reproducibility improves. As a result of precisely controlling hydrophilicity of the particle surface, detection sensitivity improves corresponding to the decrease in coarse particles and test reproducibility improves considerably.

DESCRIPTION OF EMBODIMENTS

Figure 1:
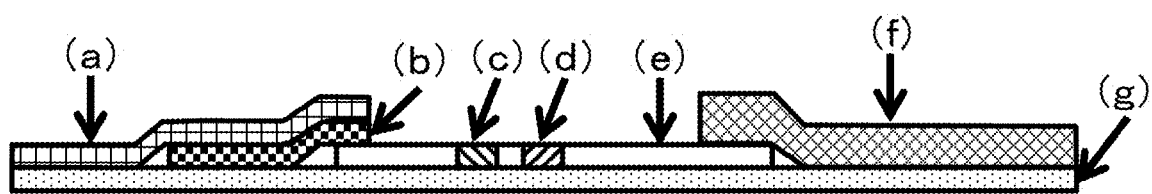
FIG. 1 is a cross-sectional view of an immunochromatographic diagnostic kit of the lateral flow type as one embodiment of the present invention.

The following provides a detailed explanation of embodiments of the present invention.

The organic colored microparticles according to the present embodiment having an average particle diameter of 100-650 nm, coloring intensity of 1.0-10.0, and when a total of 100,000 particles are detected over a range of particle diameter of 400 nm to 12000 nm, the prevalence of coarse particles having a particle diameter of 700 nm or more is 5% or less, and sphericity as represented by major axis (L)/minor axis (D) is 1.0-2.5.

The term "organic colored microparticles" in the present embodiment refers to a particulate substance that is insoluble in water or buffer solution and is loaded with coloring matter or dye. Although there are no particular limitations on the material that composes the particles, examples of such organic colored microparticles include colored latex particles obtained by coloring styrene-based latex such as polystyrene latex or an acrylic acid-based latex, colored silica particles obtained by coloring silica comprised of a three-dimensional structure comprised of silicon atoms and oxygen atoms, and coloring particles obtained by directly granulating a colored component such as colored cellulose particles obtained by coloring cellulose. The aforementioned organic colored microparticles may also be fluorescent particles. Colored cellulose particles are preferable based on the ease of adjusting the properties thereof such as adjustment of particle diameter, adjustment of color depth, adjustment of color type or adjustment of particle surface status. As a result of having a large number of hydroxyl groups, cellulose demonstrates high hydrophilicity, superior dispersion stability, and is able to contain a large amount of colored component.

There are no particular limitations on the "organic colored microparticle production method". Examples of such methods include a method consisting of first molding organic particles followed by loading a colored component such as a coloring matter or dye, a method consisting of molding particles and loading with smaller coloring particles such as metal colloids or pigment, and a method consisting of molding particles by adding together with a colored component such as a coloring matter, dye, pigment or metal colloids during particle molding. Among these, the method consisting of first molding the particles followed by loading with a colored component such as a coloring matter or dye is preferable from the viewpoint of facilitating adjustment of particle properties such as adjustment of particle diameter, adjustment of color depth, adjustment of color type or adjustment of particle surface status. A dye is preferable for the loaded colored component due to the ease of loading thereof.

A reactive dye is preferable in the case of using a dye as a coloring component. In the case of using a dye such as a direct dye, metal complex dye, acidic dye, basic dye, disperse dye, sulfur dye, vegetable dye, naphthol dye or fluorescent dye, there is the risk of not being able to obtain high coloring intensity and discoloration even if strongly dyed. However, in the case of using a reactive dye, the dye may be combined with a dye such as a direct dye, metal complex dye, acidic dye, basic dye, disperse dye, sulfur dye, vegetable dye, naphthol dye or fluorescent dye.

The reactive dye preferably has a pyrimidine structure or triazine structure. A pyrimidine structure or triazine structure has been determined to make the particles hydrophobic and have a considerable effect on hydrophilicity to be subsequently described. There are no particular limitations on the reactive dye provided it has a pyrimidine structure or triazine structure, and reactive dyes such as members of the Sumifix series, Sumifix HF series, Sumifix Supra series (which are all registered trademarks of Sumitomo Chemical Co., Ltd.) or members of the Levafix series (registered trademark of the Dystar Group) can be used. These reactive dyes enable preferable dyeing even in the case of using highly concentrated sodium hydroxide. In the case of a reactive dye not having a pyrimidine structure or triazine structure for the reactive site, when highly concentrated sodium hydroxide is used, the reactive site ends up being deactivated prior to reacting with the hydroxyl groups of the cellulose thereby preventing the attaining of desired coloring intensity and hydrophilicity. In the present embodiment, as a result of dyeing organic particles using a reactive dye having a pyrimidine structure or triazine structure for the reactive site, all of the particles are uniformly dyed, particle diameter is uniform and hydrophilicity to be subsequently described is attained.

In the case of having first molded cellulose particles followed by loading a coloring component, there are no particular limitations on the "cellulose particle molding method". Examples of this method include a method consisting of physically fragmenting natural cellulose with a ball mill or high-pressure homogenizer, a method consisting of fragmenting by chemically treating with acid or base, and a method consisting of initially dissolving cellulose in a good solvent followed by molding into the form of particles. Derivatized cellulose may also be dissolved and formed into particles followed by returning the derivatized substituents to hydroxyl groups to prepare cellulose particles. These molding methods may also be used in combination. There are also no particular limitations on the "type of cellulose", and cellulose such as regenerated cellulose, purified cellulose, natural cellulose, the aforementioned derivatized cellulose or cellulose obtained by returning derivatized substituents to hydroxyl groups can be used. Among these, the method consisting of dissolving in a good solvent followed by molding into the form of particles is preferable from the viewpoints of facilitating adjustment of particle diameter or adjustment of particle shape, and regenerated cellulose is preferable for the type of cellulose.

In the case of dissolving cellulose in a good solvent followed by molding into the form of particles, there are no particular limitations on the "type of good solvent that dissolves cellulose", and various good solvents capable of dissolving cellulose can be used, such as cuprammonium solution, viscose solution, N-methylmorpholine or various types of ionic liquids. Among these, cuprammonium solution is preferable from the viewpoint of adjustment of particle diameter and adjustment of particle shape. There are also no particular limitations on the method used to mold the dissolved cellulose into particles, and a method using phase separation was selected in the present embodiment.

The "average particle diameter" of the organic colored microparticles refers to the volume average median diameter in the case of having measured by dynamic light scattering, and the volume average median diameter is within the range of 100-650 nm. If the average particle diameter is within this range, the TL in the case of using as an immunochromatographic diagnostic kit becomes darker due to the large surface area of the particles, or in other words, analytical sensitivity becomes higher. If the average particle diameter is excessively small, surface area becomes small and analytical sensitivity may decrease or particle aggregation may occur. For this reason, the average particle diameter is preferably 150 nm or more and more preferably 200 nm or more. If particle diameter is excessively large, since the particles clog the pores of the nitrocellulose or other chromatographic medium, the portion of the nitrocellulose that inherently ought to become white after testing is colored, which may have a detrimental effect on determination of test results or worsen the detection limit. For this reason, the average particle diameter is preferably 600 nm or less and more preferably 550 nm or less. The average particle diameter described here merely refers to the average value, and a portion of the particle diameter distribution may be outside the aforementioned ranges.

The reason for using volume average to evaluate particle diameter is that, although excessively large particles end up clogging the nitrocellulose or other chromatographic medium in immunochromatographic diagnostic kits, even if only a slight number of particles having a large volume average diameter are present, the effect thereof is reflected in the result. Although there are various other criteria, such as number average or area average, for evaluating particle diameter in addition to volume average, values for particle diameter naturally vary if a different evaluation method is used.

There are no particular limitations on the CV value of the average particle diameter of the organic colored microparticles of the present embodiment. However, a value of 30% or less is preferable in the case of using as a diagnostic reagent. If the CV value of average particle diameter exceeds 30%, a detrimental effect on accuracy of diagnose during use as a diagnostic reagent appears, and as such, the CV value is more preferably 25% or less and even more preferably 20% or less. Although the accuracy of diagnosis generally improves as the CV value of average particle diameter decreases, since production complexity and costs ends up increasing if the CV value is excessively small, the CV value is preferably 1% or more in consideration of the balance between cost and accuracy.

The term "coloring intensity" refers to the value that defines the depth of color of the particles. The method used to measure coloring intensity is as indicated below.

A pure water dispersion of organic colored microparticles of a known concentration is prepared, visible absorbance is measured using an integrating sphere over a range of 400-800 nm using an optical path length of 10 mm, the peak value (ABS) of the resulting absorbance curve is measured, the resulting value is divided by the weight percentage of the organic colored microparticles, and that value is converted to absorbance per 0.01 wt % of coloring particles and defined as coloring intensity. For example, in the case the density of the prepared organic colored microparticles is 0.0045% and the peak value of the absorbance curve is 1.0, then coloring intensity becomes $(1 \times 0.01) \div 0.0045 = 2.2$.

The reason for measuring visible absorbance using an integrating sphere to measure color depth of the particles is that enables color depth of particles dispersed in a liquid to be measured with the greatest accuracy. Although there is also a method for measuring particle color depth that consists of drying the particles and measuring the resulting solid with a colorimeter, this type of method does not allow the color depth of the particles to be measured accurately. For example, metal colloids have different color tone and maximum wavelength corresponding to particle diameter, and color depth when dispersed in a liquid in the state of a dried aggregate cannot be accurately reflected. Color depth decreases when aggregation occurs even if dispersed in a liquid at the same particle concentration. The reason for using an integrating sphere when measuring visible absorbance is to eliminate the effect caused by scattering of the particles per se. Although a method that measures transmitted light is normally used to measure visible absorbance, not only the effect resulting from absorption by a coloring component relative to the incident light, but also the effect caused by scattering of the particles per se, end up being reflected in the measurement. For example, although there are cases in which the gold colloids commonly used in immunochromatography have a particle diameter of 40 nm to 60 nm and occasionally 100 nm, since each of these particle diameters is small, there is hardly any effect attributable to scattered light. In contrast, polystyrene latex particles have a large particle diameter and clearly the effect of scattered light is considerable. For the aforementioned reasons, measurement of visible absorbance using an integrating sphere is employed in order to more accurately reflect the color density of the particles per se in the case particle diameters or particle materials are different.

The "coloring intensity" of the organic colored microparticles of the present embodiment is 1.0-10.0. Particle color depth increases as this value becomes larger and analytical sensitivity is high in the case of using as an immunochromatographic diagnostic kit. Naturally, the greater the value of coloring intensity the better, and methods can be employed that use a dye of a deeper color, increase the number of dyeing times, link the particles through some form of chemical compound as a spacer, facilitate the penetration of dye by increasing the amorphous region of the particles, or facilitate the penetration of dye by making the particles porous. However, when considering economy, the upper limit of coloring intensity is preferably 7.0 or less and more preferably 5.0 or less. Since analytical sensitivity decreases in the case of using as an immunochromatographic diagnostic kit as the value of coloring intensity becomes smaller, the lower limit thereof is preferably 1.5 or more and more preferably 2.0 or more.

The "sphericity" of the organic colored microparticles of the present embodiment refers to the value represented by the particle major axis (L)/minor axis (D), and a shape in which the lengths of the major axis (L) and minor axis (D) are nearly equal is a structure that approaches the shape of a sphere. The "sphericity" (namely, the ratio L/D represented by L D) of the organic colored microparticles of the present embodiment is 1.0-2.5. Since the shape of the coloring particles becomes distorted if sphericity is outside this range, the particles end up getting caught when passing through the pores of the nitrocellulose membrane, thereby resulting in poor background. As a result, contrast with the TL becomes poor resulting in the risk of leading to misdiagnosis. Test reproducibility naturally also becomes poor. Sphericity is more preferably 1.0-2.2, even more preferably 1.0-2.0 and most preferably 1.0-1.5. The measurement method consists of capturing an electro micrograph of the particles, measuring the major axis (L) and minor axis (D) of 100 particles, and calculating the average of those 100 particles.

When a total of 100,000 of the organic colored microparticles of the present embodiment are detected over a range of particle diameter of 400 nm to 12000 nm, the prevalence of coarse particles having a particle diameter of 700 nm or more is 5% or less.

Here, "coarse particles" refer to particles having a constant distribution and a particle diameter of 700 nm or more. As a result of conducting extensive studies on coloring particles in immunochromatographic diagnostic kits, the inventors of the present invention determined that these coarse particles having a particle diameter of 700 nm or more are one of the causes of poor background of the nitrocellulose membrane. The reason for this is simply that particles having a particle diameter of 700 nm or more end up clogging the pores of the nitrocellulose membrane, thereby worsening background. If this prevalence of coarse particles exceeds 5%, background ends up being worsened considerably, and as a result thereof, contrast with the TL also becomes poor, thereby resulting in the risk of leading to misdiagnosis. From the viewpoint of developing the particles in an immunochromatographic diagnostic kit, the prevalence of the coarse particles is preferably 4.5% or less and more preferably 4.0% or less.

Although the proportion of coarse particles and the % CV of average particle diameter appear to be related at a glance, these parameters have been determined to not be linked. Although PTL3 mentions % CV, this value was obtained by observing and calculating the state of the Brownian movement of particles by dynamic light scattering as fluctuations in scattered light intensity. In other words, the average value of particle size distribution is measured. On the other hand, the proportion of coarse particles here is measured with a Coulter counter system. The Coulter counter system, which measures changes in electrical resistance between electrodes generated when particles pass through a small opening, makes it possible to directly calculate actual particle size. When the inventors of the present invention conducted evaluations with this Coulter counter system, it was found that even though particle size distribution appears narrow at a glance (small % CV), there are cases in which the proportion of coarse particles exceeds 5% depending on the particles. Since the dynamic light scattering device used in PTL3 was unable to accurately measure distribution bias, coarse particles were measured using a device employing the Coulter counter system in the present embodiment.

The "proportion of coloring component of the organic colored microparticles" refers to the proportion of a coloring component relative to the total weight of the organic colored microparticles. For example, in the case 1.0 g of organic colored microparticles is composed of 0.2 g of cellulose and 0.8 g of a coloring component, then the proportion of the coloring component is 80 wt %. The proportion of coloring component of the organic colored microparticles is preferably 10-90 wt %. If within this range, analytical sensitivity is high in the case of using as an immunochromatographic diagnostic kit. In the case of using particles obtained by dyeing cellulose with a dye as coloring particles, suitable hydrophilicity can be imparted to the cellulose by allowing the cellulose to retain an amount of dye within this range, thereby enabling a substance that specifically binds to a detected substance such as antibody to be retained by adsorption. Naturally, in addition to retaining a detected substance by adsorption, it is also possible to retain a substance that specifically binds to a detected substance by covalent bonding by introducing carboxyl groups or amino groups to colored cellulose particles. In the case the proportion of colored component is low, it is not possible to demonstrate adequate coloring intensity and analytical sensitivity becomes low in the case of using as an immunochromatographic diagnostic kit. In the case of using particles obtained by dyeing cellulose with a dye as organic colored microparticles, there are cases in which the amount of substance that specifically binds to a detected substance increases as a result of increasing the proportion of colored component. From this viewpoint, the lower limit of the proportion of coloring component of the organic colored microparticles is preferably 20 wt % or more and more preferably 30 wt % or more. Although there are no particular problems even if the proportion of colored component exceeds 90 wt %, when considering economic factors, the proportion of coloring component is preferably 85 wt % or less and more preferably 80 wt % or less.

Calculating the change in weight before and after coloring can be used as a "method for calculating the proportion of coloring component of the organic colored microparticles". In cases in which it is difficult to calculate this proportion from a change in weight, a procedure for separating the coloring component from the particles can be carried out and the proportion of coloring component can be calculated by isolating the coloring component or particles. For example, in the case of having dyed cellulose particles with a reactive dye, the proportion of coloring component can be calculated by severing the covalent bonds between the cellulose and dye with acid or base and recovering the cellulose particles by centrifugation. The proportion of coloring component can also be calculated by dissolving only the cellulose using cellulase.

Calculating the cellulose-derived component from the aforementioned proportion of coloring component of the organic colored microparticles can be used as a "method for calculating the cellulose-derived component of the organic colored microparticles". In other words, the cellulose-derived component can be calculated according to the calculation formula: "proportion of cellulose-derived component of the organic colored microparticles"=100%–(proportion of coloring component of the organic colored microparticles). The proportion of cellulose-derived component of the organic colored microparticles is preferably 90-10 wt %. If within this range, dispersion stability of the cellulose particles can be maintained. The lower limit of the cellulose-derived component of the organic colored microparticles is more preferably 15 wt % or more and particularly preferably 20 wt % or more, while the upper limit is more preferably 80 wt % or less and particularly preferably 70 wt % or less for the same reasons described for the aforementioned proportion of coloring component.

"Hydrophilicity" was measured in the present embodiment as an indicator representing the degree of hydrophobicity or hydrophilicity of the organic colored microparticles of the present embodiment. In the present description, "hydrophilicity" refers to the wettability of the surface of the microparticles, or in other words, an indicator representing affinity with water.

The hydrophilicity of the organic colored microparticles of the present embodiment is preferably within the range of 1.0-30.0. If hydrophilicity is within this range, the amount of protein or antibody adsorbed to the surface of the organic colored microparticles increases since the particle surface is hydrophobic. Since cellulose is hydrophilic and proteins and typically has difficulty in adsorbing protein or antibody, it is necessary to make the surface of the particles hydrophobic in order to adsorb protein or antibody. Conversely, the adsorbed amount can similarly be controlled by controlling the degree of hydrophobicity with this indicator. In other words, organic colored microparticles having superior reproducibility can be produced in an immunochromatographic diagnostic kit. There is no mention whatsoever regarding this indicator in PTL3 and data was indicated that lacks reproducibility. Since the surface of microparticles becomes hydrophilic if hydrophilicity is 30.0 or higher, the adsorption of protein or antibody on the surface of the microparticles ends up being impaired, and sensitivity decreases or the results end up lacking reproducibility. If hydrophilicity is less than 1.0, hydrophobicity becomes excessively strong thereby causing the antibody or protein to adsorb to the nitrocellulose membrane resulting in poor background. From the above viewpoints, the upper limit of hydrophilicity is more preferably 27.0 and even more preferably 25.0. On the other hand, the lower limit thereof is more preferably 1.5 and even more preferably 2.0.

In the case the reactive dye used to color the microparticles contains elemental fluorine (F), the elemental fluorine (F) remains on the surface of the organic colored microparticles of the present embodiment. In the organic colored microparticles of the present embodiment, the relative element concentration of elemental fluorine (F) on the particle surface as calculated by measuring by X-ray photoelectron spectroscopy (XPS) is preferably 0.1 atomic % or more. If the relative element concentration of elemental fluorine (F) is within this range, sensitivity and reproducibility surprisingly improve when protein or antibody is adsorbed on the surface of the organic colored microparticles. The lower limit of the relative element concentration of elemental fluorine (F) on the surface of the organic colored microparticles of the present embodiment is preferably 0.2 atomic % or more and more preferably 0.3 atomic % or more.

An "immunochromatographic diagnostic kit" containing the organic colored microparticles of the present embodiment as an element thereof refers to that which easily detects the presence or absence of a test target substance in various specimens using an antigen-antibody reaction. The types of these diagnostic kits consist of a lateral flow type and a flow through type. Although there are no particular limitations on the type of kit provided coloring particles (organic colored microparticles) and a sample pad are used, a lateral flow type is preferable. Although lateral flow types consist of a dipstick type and a cassette type, there are no particular limitations thereon. There are no particular limitations on the composition of the diagnostic kit and a composition may be employed that is commonly used in the art. There are no particular limitations on members other than the conjugate pad (b) containing antibody-sensitized coloring particles and the sample pad (a) provided they are commonly used in the art, and examples thereof include the chromatographic medium (e), absorbent pad (0 and mount (g) shown in FIG. 1. A portion of these members may be omitted as necessary. An example of the structure is the structure like that described in FIG. 1 of PTL1. FIG. 1 attached to the present description is merely an example and does not limit the present embodiment in any way.

As indicated by (a) in FIG. 1, the "sample pad" refers to the portion that initially receives the specimen serving as the measurement target in immunochromatography. Typical examples of sample pads include cellulose filter paper, paper, fiberglass, glass fiber, acrylic fiber, nylon fiber and various woven materials.

In order to control the hydrophilicity/water repellency and water absorption ratio of the sample pad, various types of agents or powders may be contained in a nonwoven fabric comprised of regenerated cellulose fibers, or a portion of the cellulose may be derivatized, provided there are no detrimental effects on the aforementioned properties and they are contained are within a range that does not have an effect on the antigen-antibody reaction or antibody stability. Examples of impregnated agents include surfactants, proteins, antibodies, resins, water-soluble polymers, antibacterial agents, preservatives and antioxidants. Examples of cellulose derivatization include carboxymethylation, carboxyethylation, primary amination, secondary amination, tertiary amination, quaternary amination and oxygenation.

The sample pad may be pretreated as necessary. For example, pretreatment may be carried out by preliminary containing a buffer, surfactant, protein, reagent that traps contaminants in the specimen sample, preservative, antibacterial agent, antioxidant or desiccant. Although there are no particular limitations on the shape of the sample pad, with respect to the size of the sample pad, for example, the length (length in the direction liquid flows) is preferably about 10-25 mm in consideration of connectedness with the specimen liquid and diagnosis time, while there are no particular limitations on width (direction perpendicular to the flow of liquid) provided it is greater than the width of the conjugate pad. If the width is excessively narrow, there is the possibility of the test liquid moving around the edges of the sample pad.

The "conjugate pad" refers to a pad containing a conjugate that contains coloring particles (organic colored microparticles), and for example, contains coloring particles bound with antibody that binds to a test target substance. There are no particular limitations on the material of the conjugate pad, and ordinary glass fiber or resin fiber can be used. Although resin fibers such as polyolefin fibers such as polyethylene fibers, polyester fibers, polyamide fibers or acrylic-based fibers, or conjugated fibers of these resin fibers, can be preferably used as resin fibers, the resin fibers are not limited thereto. A conjugate pad made of resin fiber is preferable in consideration of the work environment. Among conjugate pads made of resin fiber, those made of a material that is hydrophobic to a certain degree are preferable when considering from the viewpoint of facilitating release of the coloring particles. The conjugate pad may be used after pretreating with a surfactant in the case hydrophobicity is excessively high. A conjugate pad made of polyethylene resin that has been treated with surfactant is more preferable.

A "diagnosis method" that uses the immunochromatographic diagnostic kit of the present embodiment refers to various diagnoses made using the immunochromatographic diagnostic kit. There are no particular limitations on the diagnosis target, and the diagnosis method can be used to test various diagnosis targets such as human, animal, food, plant and other environmental tests. In an ordinary diagnosis procedure, a specimen sample is collected from a test subject, the sample is subjected to pretreatment such as extraction or filtration as necessary, the sample is dropped onto the sample pad, and the result of the diagnosis is determined according to coloring that differs depending on the presence or absence of a test target substance after having waited a prescribed amount of time from the start of the test. Naturally, the procedure is not limited thereto, but rather this diagnosis method can be used for diagnoses using similar procedures and principles. The specimen sample can be removed of superfluous foreign matter and contaminants by filtering in advance, thereby making it possible to expect even faster diagnosis and improved diagnostic accuracy.

In the present embodiment, in addition to a method consisting of dropping a specimen directly onto the sample pad, the specimen may be dropped onto the sample pad after having diluted to an arbitrary dilution factor with a specimen pretreatment liquid adjusted in advance to a prescribed composition. The purpose of the use of a specimen pretreatment liquid is to add, for example, a component for facilitating reaction with antigen in the specimen, a component that suppresses non-specific reactions, a component that facilitates the flow of coloring particles, or a component that suitably aggregates the coloring particles and improves visibility during the capture thereof at the test line. For example, a buffer, protein, inorganic salt, water-soluble polymer, reducing agent or chelating agent may be added. In the case of using coloring particles like those of the invention of the present application in particular, the addition of a nonionic surfactant, various types of water-soluble amino acids, proteins, inorganic salts or water-soluble polymers is preferable. Although the specific types and added amounts of components vary according to the type of test target and antibody used, examples of nonionic surfactants include poly(oxyethylene) alkyl ether, poly(oxyethylene) octyl phenyl ether and poly(oxyethylene) nonyl phenyl ether. Examples of water-soluble amino acids include asparagine, aspartic acid, alanine, arginine, isoleucine, glycine, glutamine, glutamic acid, cysteine, serine, tyrosine, tryptophan, threonine, valine, histidine, proline, phenylalanine, methionine, lysine and leucine. Examples of proteins include casein, skim milk, casein hydrolysate, bovine serum albumin and fish gelatin. Compounds that generate alkaline metal ions such as sodium, potassium or lithium are preferable as inorganic salts. Polyethylene glycol, polyvinyl alcohol, polyvinylpyrrolidone, carboxymethyl cellulose and other cellulose derivatives are preferable as water-soluble polymers. These components may not only be added to a specimen treatment liquid, but may also be preliminarily added to the sample pad, conjugate pad or chromatographic medium (nitrocellulose membrane).

There are no particular limitations on the target capable of being diagnosed with the immunochromatographic diagnostic kit, and specific examples thereof include cancer markers, hormones, infectious diseases, autoimmunity, plasma proteins, TDM, coagulation/fibrinolysis, amino acids, peptides, proteins, genes and cells. Specific examples include CEA, AFP, ferritin, β2 microglobulin, PSA, CA19-9, CA125, BFP, elastase 1, pepsinogen 1,2, occult blood, urine β2 microglobulin, PIVKA-2, urine BTA, insulin, E3, HCG, HPL, LH, HCV antigen, HBs antigen, HBs antibody, HBc antibody, HBe antigen, HBe antibody, HTLV-1 antibody, HIV antibody, HIV antigen, HIV virus gene, toxoplasma antibody, syphilis, ASO, influenza A antigen, influenza A antibody, influenza B antigen, influenza B antibody, rotavirus antigen, adenovirus antigen, rotavirus/adenovirus antigen, group A *streptococcus*, group B *streptococcus*, *Candida* antigen, *Clostridium difficile* (CD), *Cryptococcus* antigen, *Vibrio cholerae*, meningococcus antigen, granulocytic elastase, *Helicobacter pylori* antigen, O157 antigen, O157 antibody, leptospira antibody, aspergillusantigen, MRSA, RF, total IgE, LE test, CRP, IgG, A, M, IgD, transferrin, urine albumin, urine transferrin, myoglobin, C3/C4, SAA, LP(a), α1-AC, α1-M, haptoglobin, microtransferrin, APR score, FDP, D dimer, plasminogen, AT3, α2PI, PIC, PAI-1, protein C, coagulation factor X3, type IV collagen, hyaluronic acid, GHbA1c, various other types of antigens, various types of antibodies, various types of viruses, various types of bacteria, various types of amino acids, various types of peptides, various types of proteins, various types of DNA, various types of cells, various types of allergens, various types of residual agricultural chemicals and various types of harmful substances.

Although coloring particles (organic colored microparticles) are required to load a substance that specifically binds to a detected substance such as antibody, there are no particular limitations on the loading method. Examples of loading methods include loading by physical adsorption, loading by covalent bonding and loading by a combination thereof. There are no particular limitations on the type or amount of loaded substance. Antibody is the most common and preferable for use as the type of loaded substance. Although loading by physical adsorption is preferable for the loading method from the viewpoint of ease of the procedure, loading by covalent bonding is preferable from the viewpoints of stability and performance.

There are no particular limitations on the chromatographic medium used in the immunochromatographic diagnostic kit, and various commonly used chromatographic media can be used. A more specific example is a nitrocellulose membrane. Although commercially available nitrocellulose membranes are classified according to the time required to move a fixed distance referred to as flow rate, a faster flow rate indicates a larger pore size. In the present invention, a membrane having a large pore size is preferable since it demonstrates a faster flow rate and is less susceptible to clogging of the coloring particles. More specifically, the membrane preferably has a flow rate of greater than 180 sec/4 cm.

Although the following provides a description of examples of a cellulose particle production method for producing cellulose particles as organic colored microparticles, a cellulose particle coloring method and an immunochromatographic diagnostic kit production method, the present invention is naturally not intended to be limited thereto.

[Cellulose Particle Production Method]

Cellulose linter is dissolved in a good solvent of cellulose. In the present invention, a cuprammonium solution prepared using a known method is used for the good solvent. A mixture of organic solvent, water and ammonia is mainly used for the coagulation liquid. The prepared cuprammonium cellulose solution is added while stirring this coagulation liquid to carry out coagulation.

The important point here is to preliminarily incubate the cuprammonium cellulose solution in the presence of air to adjust the average degree of polymerization of the cellulose in the cuprammonium cellulose solution. The proportion of coarse particles having a particle diameter of 700 nm or more will not be 5% or less if the average degree of polymerization (DP) of the cellulose is not adjusted. Consequently, in the present embodiment, the average degree of polymerization of the cellulose in the cuprammonium cellulose solution is adjusted to 50-400. If the average degree of polymerization is less than 50, it becomes difficult to form the shape of the particles thereby preventing the particles from having the target sphericity. On the other hand, if the average degree of polymerization (DP) exceeds 400, the amount of coarse particles becomes excessively large thereby causing defective development and poor background when using in immunochromatography. As a result, contrast with the TL may become poor thereby having the potential for leading to misdiagnosis. The lower limit of the average degree of polymerization (DP) is preferably 60 or more and more preferably 70 or more from the viewpoint of particle formation. The upper limit is preferably 350 or less and more preferably 300 or less from the viewpoint of controlling the generation of coarse particles.

The average degree of polymerization of cellulose refers to the value obtained by measuring specific viscosity of a dilute cellulose solution obtained by dissolving cellulose microparticles in Cadoxen with an Ubbelohde viscometer and calculating from the limiting viscosity number [η] thereof using the following viscosity formula and conversion formula described in the reference literature: Eur. Polym. J., 1, 1 (1996).

Viscosity formula: $[\eta] = 3.85 \times 10^{-2} \times M_W^{0.76}$

Conversion formula: $DP = M_W / 162$

Following coagulation, sulfuric acid is added to carry out neutralization and regeneration and allow the obtaining of a slurry containing the target cellulose particles. At this time, the slurry is acidic due to the presence of residual acid used for regeneration, and since it contains impurities such as ammonium salt generated during neutralization, a procedure is required for purifying to a cellulose dispersion comprised of the cellulose particles and medium. In the present embodiment, repeated dilution treatment using centrifugation, decantation and a dispersion medium liquid is used for this purification procedure. Since the cellulose particles in the resulting cellulose particle dispersion may aggregate during the course of the purification procedure, dispersion treatment can be carried out by shearing in this case. In the present embodiment, a high-pressure homogenizer is used as a means for imparting shear.

[Cellulose Particle Coloring Method]

A reactive dye having a pyrimidine structure or triazine structure is added after having added a highly concentrated aqueous sodium hydroxide solution to the resulting cellulose particle slurry followed by heating to the prescribed temperature with a constant temperature bath while stirring with a magnetic stirrer. A slurry containing the target dyed cellulose particles can be obtained after a prescribed amount of time has elapsed. Since individual particles can each be uniformly dyed on the basis of this process, although the particles obtained in PTL3 have an irregular contour or jagged surface, the irregular contour and jagged surface of the particles obtained in the present embodiment are greatly improved and sphericity is markedly better. The entirety of the particles was found to be able to be dyed as if the surface had been coated when dyed using the dyeing method employing a reactive dye as previously described. At the same time, this method was determined to enable particle diameter to increase uniformly, or in other words, enable the generation of particles having an extremely large particle diameter to be suppressed, perhaps due to individual particles being uniformly coated. Elemental fluorine (F) was also determined to be present on the surface of the particles. In contrast, although dyeing was carried out using sodium carbonate instead of highly concentrated sodium hydroxide in PTL3, since the ability of sodium carbonate to cause swelling of cellulose is weaker in comparison with sodium hydroxide, only the outermost surface of those particles susceptible to swelling swells and ends up reacting with the reactive dye, thereby preventing a uniform reaction from occurring from the perspective of all particles. In PTL3, an elimination reaction is observed for a portion of the dye as a result of washing with sodium hydroxide after having initially dyeing the particles, thereby causing an excessive loss of surface uniformity. In this manner, in PTL3, the previously described coating of the surface with dye is not uniform, a satisfactory degree of sphericity is unable to be obtained, and hydrophilic cellulose is exposed on the surface, thereby preventing hydrophilicity from being lowered. When dyed using sodium carbonate, it was determined that the amount of coarse particles ends up increasing perhaps due to the large, non-uniform surface area, or in other words, dyeing proceeding starting with those particles having a large particle diameter. Elemental fluorine (F) on the particle surface also ends up being eliminated due to repeated washing with base. For this reason, the inventors of the present invention employed a dyeing method that uses highly concentrated sodium hydroxide that enables individual particles to be uniformly dyed throughout from the core to the surface thereof. As a result, the particles were able to be uniformly dyed with dye, particle sphericity was able to be markedly improved, hydrophilicity was able to be lowered, and the number of coarse particles was able to be reduced.

As a result of dyeing with a reactive dye having a pyrimidine structure or triazine structure, which exhibits high reactivity and is resistant to base, in the presence of highly concentrated sodium hydroxide, the particles can be dyed uniformly and hydrophilicity can be reduced considerably.

Purification by centrifugation is then carried out to obtain a dyed cellulose particle dispersion. Since the cellulose particles in the resulting dyed cellulose particle dispersion may aggregate during the course of the purification procedure, dispersion treatment by shearing can be carried out in this case. In the present embodiment, a high-pressure homogenizer is used as a means for imparting shear. Subsequently, various properties of the resulting colored cellulose particles are measured.

[Immunochromatographic Diagnostic Kit Production Method]

A dispersion of colored cellulose particles adjusted to a prescribed concentration is prepared, buffer and antibody are added and stirring is carried out for a certain amount of time while adjusting temperature to adsorb the antibody to the colored cellulose particles. After stirring for a certain amount of time, a blocking agent is added followed stirring for a certain amount of time while adjusting temperature to block the colored cellulose particles. The blocking here refers to a procedure for coating the particles alone or particles loaded with antibody or antigen. Various blocking agents can be used for the blocking agent corresponding to the test target substance, specimen or composition of the solution obtained by the dilution thereof. Casein is particularly preferable as a colored cellulose blocking agent. In this case, casein coats antibody present within the colored cellulose particles loaded with antibody as well as the surface of the colored cellulose particles. Centrifugation is carried out to wash the colored cellulose particles following antibody adsorption and blocking, supernatant containing surplus antibody and blocking agent is separated from the settled particles, and the supernatant is removed by decantation. A liquid such as a buffer solution is added to the settled particles and dispersion treatment is carried out by ultrasonic dispersion as necessary. Washing using a series of procedures consisting of sedimentation by centrifugation, removal of supernatant and addition of liquid is carried out the required number of times to prepare a dispersion containing a prescribed concentration of particles that have undergone antibody adsorption and blocking. Protein, surfactant and sugar such as sucrose or trehalose are added to this dispersion as necessary followed by coating the resulting solution on a polyethylene conjugate pad and drying to prepare a portion containing a detection reagent. A regenerated cellulose continuous long fiber nonwoven fabric is then coated with buffer, surfactant, protein, reagent that traps contaminants present in the specimen sample, preservative, antibacterial agent, antioxidant or desiccant as necessary followed by drying to prepare the sample pad. A chromatographic medium made of a porous nitrocellulose membrane on which antibody has been immobilized at a prescribed location, and an absorbent pad made of cellulose filter paper for absorbing the specimen, are prepared. These are then immobilized on a mount having an adhesive site referred to as a backing sheet followed by cutting to a prescribed size to produce an immunochromatographic diagnostic kit.

EXAMPLES

Although the following provides a more detailed explanation of the present invention through examples thereof, the present invention is not limited to only these examples. Unless specifically mentioned otherwise, all procedures were carried out in an environment at a temperature of 23° C. and relative humidity of 55% RH. The following measurement and calculation methods were used in the examples.

[Measurement of Average Degree of Polymerization of Cellulose Microparticles]

The average degree of polymerization (DP) of cellulose refers to the value obtained by measuring specific viscosity of a dilute cellulose solution obtained by dissolving cellulose microparticles in Cadoxen with an Ubbelohde viscometer and calculating from the limiting viscosity number [η] thereof using the following viscosity formula and conversion formula described in the reference literature: Eur. Polym. J., 1, 1 (1996) as previously described.

$$[\eta] = 3.85 \times 10^{-2} \times M_W^{0.76}$$

$$DP = M_W / 162$$

[Measurement of Average Particle Diameter of Coloring Particles]

The Nanotrac Particle Size Distribution Analyzer Model UPA-EX150 (dynamic light scattering method) manufactured by Nikkiso Co., Ltd. was used for the measuring instrument. A sample containing 0.01 wt % of colored organic microparticles (coloring particles) and 99.99 wt % pure water was used for the measurement sample. Measurement conditions consisted of 30 integrations and measurement time per measurement of 30 seconds, and the median diameter of the volume average particle diameter distribution was taken to be the average particle diameter. CV value was calculated by using the standard deviation of the particle size distribution and average particle diameter obtained from 30 integrations.

[Measurement of Coloring Intensity of Coloring Particles]

A device employing the JASCO V-650 ultraviolet-visible-near infrared spectrophotometer manufactured by Jasco Corp. (optics: single monochromator, Czerny-Turner mount, double beam type, light source: deuterium lamp (190-350 nm), halogen lamp (330-900 nm)) equipped with the ISV-722 integrating sphere unit manufactured by the same manufacturer was used for the measuring instrument. A sample obtained by adjusting the concentration of an arbitrary concentration of a coloring particle dispersion or dry particles to 0.01 wt % coloring particles and 99.99 wt % pure water using distilled water was used for the measurement sample. Following adjustment of the concentration thereof, 2.5 mL of this aqueous dispersion was added to a quartz cell having an optical path length of 10 mm (volume: 3.5 mL, optical path width: 10 mm) and the quartz cell was placed in the sample holder of the ultraviolet-visible-near infrared spectrophotometer followed by carrying out the measurement. The maximum value (ABS) of the resulting absorbance peak over a visible light range of 400-800 nm was taken to be coloring intensity.

[Calculation of Proportion of Coloring Component of Colored Particles]

The proportion of coloring component of the colored particles was calculated from the weight of the coloring particles after having undergone a prescribed number of coloring procedures and the weight of the particles before coloring. For example, the coloring component in the case of having colored 1.0 g of cellulose particles and obtained 2.5 g of colored cellulose particles was calculated as 2.5 g−1.0 g=1.5 g. The proportion of the coloring component in this case becomes 1.5 g 2.5 g×100=60.0 wt %.

[Calculation of Proportion of Cellulose-Derived Component of Colored Particles]

The proportion of the cellulose-derived component was calculated according to the calculation formula: "Proportion of cellulose-derived component of colored particles"=100%−(proportion of coloring component of colored particles) as was previously described.

[Measurement of Sphericity of Coloring Particles]

The JSM-6700 Scanning Electron Microscope manufactured by JEOL Ltd. was used for the measuring instrument. A sample containing 0.01 wt % coloring particles and 99.99 wt % pure water was dropped onto a mica plate, the coloring particles were adsorbed to the mica plate by waiting 10 seconds, and excess liquid was wiped off with KimWipes followed by drying. The resulting mica plate was coated with platina to prepare a sample for electron microscope measurement. Observation was carried out at an accelerating voltage of 1.6 kV and measurement magnification of 50,000 times, the required number of images were photographed so that the number of particle images was 100 or more, and the major axis (L) and minor axis (D) of each particle were measured followed by calculating the average value of L/D for 100 particles.

[Calculation of Proportion of Coarse Particles Among Colored Particles]

Measurement was carried out using the AP20 aperture with the Multisizer 4 (Coulter counter system) manufactured by Beckman Coulter Inc. for the measuring instrument. Isoton II-PC diluent also manufactured by Beckman Coulter Inc. (sodium chloride: 7.93 g/L, sodium fluoride: 0.30 g/L, product number: 8546719) was used for the electrolyte. A sample containing 1.00 wt % colored particles and 99.99 wt % pure water was used for the measurement sample. 100 mL of Isoton II diluent were first added to a 200 mL beaker. Coloring particles were further added to this beaker so that the coloring particle concentration in the Isoton II-PC diluent was about 5%. Measurement was carried out while stirring with the stirrer provided with the Multisizer 4. The prevalence (X) of coarse particles was calculated according to the following equation from the number of particles having a particle diameter of 700 nm or more when a total of 100,000 particles were detected under measurement conditions consisting of a range of 400 nm to 12000 nm.

Prevalence of coarse particles $(X)(\%) = \{$number of particles having a particle diameter of 700 nm or more $(A)/100{,}000\} \times 100$ For example, in the case 7000 particles having a particle diameter of 700 nm or more were present among 100,000 particles, the prevalence of such particles is 7.0%. The details of the operating conditions are indicated below.

Aperture current value: 800 μA
Calibration coefficient Kd: 29.764
Amplification factor: 4
Measured particle diameter range: 400 nm to 12000 nm
Measured number of particles: 100,000
Colored particle concentration in Isoton II-PC diluent during measurement: 5%

[Measurement of Colored Particle Hydrophilicity]

Hydrophilicity is measured by pulsed NMR. Pulsed NMR is an analytical technique for measuring exciting the protons of water molecules by irradiating a microparticle dispersion with radio waves followed by measuring the amount of time until the protons return to the ground state (relaxation time). Water molecules adsorbed to the surface of the microparticles have a short relaxation time due to restriction of the mobility thereof, while bulk water molecules (water molecules not adsorbed to the surface of the microparticles) have a long relaxation time since the mobility thereof is not restricted and are able to move freely. Thus, the relaxation time of a microparticle dispersion obtained by pulsed NMR changes according to the ratio between water molecules adhered to the microparticle surface and bulk water molecules. Namely, the higher the hydrophilicity of the microparticle surface, the shorter the relaxation time since a larger number of water molecules can be adsorbed.

The Minispec mq20 system manufactured by Bruker GmbH is used to measure pulsed NMR. A microparticle dispersion having a concentration of 1% (wt/vol) is stirred followed by transferring to a 0.5 mL glass NMR tube having a diameter of 10 mm, placing in the pulsed NMR system set to 30° C., and measuring various parameters after setting as indicated below.

Observed nucleus: $^1H$
Measured relaxation time: Transverse relaxation time T2 (ms)
Measurement mode: CPMG method
Integration times: 32
Recycle delay: 10 (s)
90°-180° pulse separation (τ): 2 (ms)
Total number of acquired echoes: 2000 points The resulting magnetization decay curve (curve indicating time-based changes in magnetization intensity) was fitted according to the least squares method using the exponential approximation function of Microsoft Excel according to the following equation (1):

$$M(t)=M0 \cdot \exp(-t/T2) \quad \text{Equation (1)}$$

(wherein, M(t): signal strength at a certain time t, M0: initial value of signal strength, T2: relaxation time). T2 in Equation (1) is the relaxation time.

In order to calculate hydrophilicity from the measured relaxation time (T2), a graph is prepared by plotting the rate of change of relaxation time (Rsp value) on the vertical axis and plotting the total surface area (TSA) of the microparticles on the horizontal axis, generating an approximation straight line according to the least squares method, and determining hydrophilicity as the slope thereof.

Rsp Value Calculation Method $$Rsp \text{ value}=Rav \div Rb-1$$

(wherein, Ray: average relaxation time (reciprocal of sample relaxation time), Rb: relaxation time constant of bulk water (reciprocal of relaxation time of blank water)).

TSA Value (m$^2$) Calculation Method $$TSA \text{ value}=SA \times V \times \Psi p \times \rho$$

(wherein, SA: specific surface area of microparticles (m$^2$/g)=6÷(ρ×d), where p: microparticle density (g/cm$^3$) (where, cellulose microparticle density: 1.4 g/cm$^3$, latex particle density: 1.0 g/cm$^3$, gold colloid particle density: 19.3 g/cm$^3$), d: microparticle diameter (μm), V: volume of NMR tube of portion irradiated with radio waves (cm$^3$) (≈amount of sample), Ψp: microparticle volume ratio (where microparticle volume (i)=microparticle concentration (wt %)÷100÷microparticle density (p: same as previously defined), water volume (ii)=(1−microparticle volume (i))÷water density (0.997 g/cm$^3$), (microparticle specific volume)=microparticle volume (i)÷water density (ii)).

Figure 2:
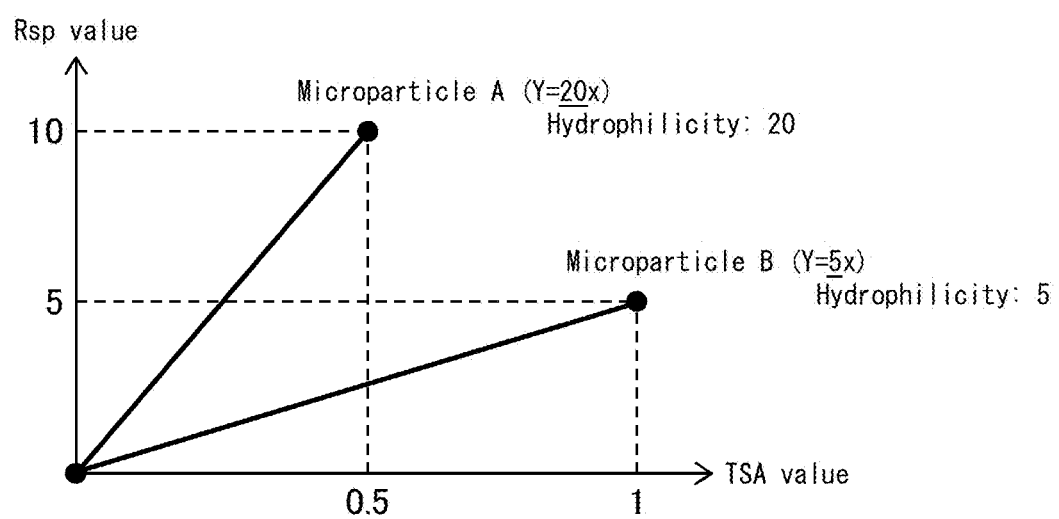
FIG. 2 is an explanatory diagram of a method for determining hydrophilicity.

For example, as shown in FIG. 2, the values for microparticle A (TSA value: 0.5, Rsp value: 10) and the values for microparticle B (TSA value: 1, Rsp value: 5) are plotted on a graph and approximation straight lines are generated according to the least squares method. Y=20× in the case of microparticle A and Y=5× in the case of microparticle B. Hydrophilicity is judged to be higher for the microparticle having the larger the slope of the approximation straight line (hydrophilicity), namely microparticle A.

[Measurement of Relative Element Concentration of Elemental F on Surface of Colored Particles]

The relative element concentration of elemental fluorine (F) on the surface of the colored particles is measured by XPS. The coloring particles were placed on a dish-shaped sample stage measuring 1.5 mm φ×0.2 mm t and measured by XPS under the conditions indicated below. XPS measurement was carried out under the following conditions using the Thermo-Fisher ESCALAB 250 system.

Excitation source: Monochromatic AlKα, 15 kV×10 mA
Analysis size: Approx. 1 mm (shape: elliptical)
Photoelectron capture angle: 0° (sample surface perpendicular to axis of spectroscope)
Capture areas:
  Survey scan: 0-1,100 eV
  Narrow scan: C1s, N1s, S2p, O1s, Na1s, F1s, Si2p, Cl2p
Pass energy:
  Survey scan: 100 eV
  Narrow scan: 20 eV The relative element concentration ([F]) of elemental fluorine (F) is determined from the integrated intensities of C1s, N1s, S2p, O1s, Na1s, F1s, Si2p and Cl2p obtained according to this measurement along with the relative sensitivity coefficient of each peak (C1s: 1.00, N1s: 1.68, S2p: 1.98, O1s: 2.72, Na1s: 10.2, F1s: 4.67, Si2p: 0.93, Cl2p: 2.285) using the equation indicated below:

$$[F](\text{atomic \%})=100 \times (1_{F1s}/RSF_{F1s})/\Sigma I_j/RSF_j)$$

(wherein, $1_{F1s}$: integration intensity of F1s (eV·cps), $RSF_{F1s}$: relative sensitivity coefficient of F1s, $I_j$: integration intensity of C1s, N1s, S2p, O1s, Na1s, F1s, Si2p and Ci2p (eV·cps), RSFj: relative sensitivity coefficient of C1s, N1s, S2p, O1s, Na1s, F1s, Si2p and Ci2p).

[Measurement of Diagnosis Time and Reproducibility of Immunochromatographic Diagnostic Kit]

An immunochromatographic diagnostic kit cut to a width of 5 mm was placed in a plastic housing. The resulting diagnostic kit contained in the housing was measured using the Immunochromato-Reader C10066-10 manufactured by Hamamatsu Photonics K.K. The device was set corresponding to the color of the particles used. Human chorionic gonadotropin (hCG) was used for the test target substance, and the hCG was diluted with 66 mM, pH 7.4 phosphate buffer solution (PBS) containing 1 wt % of bovine serum albumin (BSA) to prepare a positive specimen having an hCG concentration of 10 mIU/ml. 120 μl of this positive specimen were dropped onto the sample dropping portion of the diagnostic kit followed by measurement with the Immunochromato-Reader every 20 seconds to measure coloring time of the TL. The reason for measuring every 20 seconds is that each measurement takes under 20 seconds. The time during which the coloring intensity (units: mABS) of the TL obtained with the Immunochromato-Reader became 20 mABS or more was measured. The reason for using 20 mABS is that, although there are individual differences, the presence of the TL can be visualized with the naked eye if coloring intensity is 20 mABS or more. This measurement was carried out 20 times, the average value of the resulting values was taken to be the diagnosis time and the standard deviation thereof was taken to be the diagnosis time standard deviation. The indicator % CV representing reproducibility was calculated according to the equation indicated below.

% $CV$=(diagnosis time standard deviation/diagnosis time)×100

[Measurement of Sensitivity and Reproducibility of Immunochromatographic Diagnostic Kit]

120 μl of the positive specimen were similarly dropped onto the sample dropping portion of the diagnostic kit and coloring intensity of the TL was measured with the Immunochromato-Reader after waiting for 15 minutes. This measurement was carried out 20 times, the average value of the resulting values was taken to be TL intensity, and the standard deviation thereof was taken to be the standard deviation of Tl intensity. The indicator % CV representing reproducibility was calculated according to the equation indicated below.

% $CV$=($TL$ intensity standard deviation/$TL$ intensity)×100

[Measurement of Background of Immunochromatographic Diagnostic Kit]

120 μl of the positive specimen were similarly dropped onto the sample dropping portion of the diagnostic kit followed by measuring the background intensity 2 mm upstream from the TL and background intensity 2 mm downstream from the TL with the Immunochromato-Reader after waiting for 15 minutes. The average value thereof was taken to be the background intensity.

[Measurement of False Positivity of Immunochromatographic Diagnostic Kit]

A negative specimen was prepared by preparing 66 mM, pH 7.4 PBS containing 1 wt % BSA. 120 μl of the negative specimen were dropped onto the sample dropping portion of the diagnostic kit followed by measuring coloring intensity of the TL with the Immunochromato-Reader after waiting for 15 minutes. This measurement was carried out 5 times and the diagnostic kit was judged to not demonstrate false positivity if the average value of the resulting values was 5 mABS or less. The reason for using 5 mABS is that, although there are individual differences, the presence of the TL cannot be visualized with the naked eye if coloring intensity is 5 mABS or less.

[Measurement of Detection Limit of Immunochromatographic Diagnostic Kit]

False specimens were prepared in which hCG concentration was decreased in a stepwise manner from 3.20 IU/ml to 1.60 mIU/ml, 0.80 mIU/ml, 0.40 mIU/ml, 0.20 mIU/ml, 0.10 mIU/ml, 0.05 mIU/ml and 0.025 mIU/ml. 120 μl were similarly dropped onto the sample dropping portion of the diagnostic kit followed by measuring coloring intensity of the TL with the Immunochromato-Reader after waiting for 15 minutes. This measurement was carried out 5 times for each concentration, the result was judged to be positive in the case the average value of the resulting values was 20 mABS or more above the value obtained during measurement of the negative specimen, while the result was considered to be equal to or below the detection limit in the case it was equal to or lower than the level thereof. The lower limit of hCG concentration for which a positive judgment was obtained was taken to be the detection limit.

Example 1

A cuprammonium cellulose solution was prepared using a method known in the prior art having a cellulose concentration of 0.37 wt %, copper concentration of 0.13 wt % and ammonia concentration of 1.00 wt %. The resulting cuprammonium cellulose solution was stirred slowly in the presence of air to adjust the degree of polymerization over the course of 12 hours. A coagulation liquid was prepared having a tetrahydrofuran concentration of 89.00 wt % and water concentration of 11.00 wt %. 500 g of the prepared cuprammonium cellulose solution were added while slowly stirring 5000 g of the coagulation liquid using a magnetic stirrer. After continuing to stir for about 5 seconds, 1000 g of 10 wt % sulfuric acid were added to carry out neutralization and regeneration and obtain 6500 g of a slurry containing cellulose microparticles.

The resulting slurry was centrifuged for 10 minutes at a speed of 10000 rpm. The sediment was removed by decantation and distilled water was injected and stirred followed by repeating centrifugation. This procedure was repeated several times until the pH reached 6.0-7.0 followed by carrying out dispersion treatment with a high-pressure homogenizer to obtain 150 g of a cellulose microparticle dispersion. As a result of measuring the average particle diameter of the resulting cellulose microparticles, the average particle diameter was determined to be 261 nm. Measurement of the degree of polymerization of the microparticles yielded a value of 110.

Figure 3:
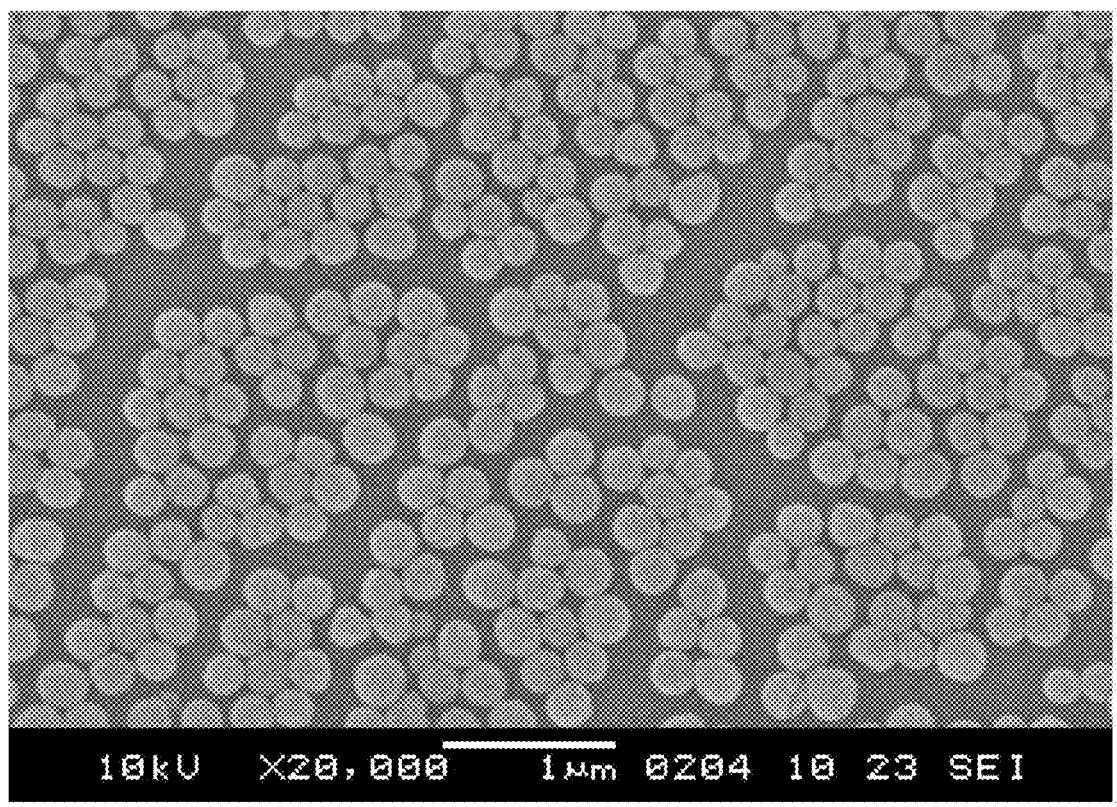
FIG. 3 is an electron micrograph of colored cellulose microparticles obtained in Example 1.

Next, the cellulose microparticles prepared in the manner described above were dyed. 30 g of sodium sulfate and 1.00 g of a reactive dye having a triazine structure (Levafix Red CA GR® manufactured by Dystar) were added to 100 g of the cellulose microparticle dispersion adjusted to a microparticle concentration of 1.00 wt % followed by heating to 60° C. using a constant temperature bath while stirring. After heating to 60° C., 10 g of sodium hydroxide were added followed by dyeing for 2 hours. The resulting crude colored microparticles were subjected to up to a total of five cycles of a series of procedures consisting of washing with deionized water, recovering by centrifugation and subsequently recovering by centrifugation to obtain colored cellulose microparticles. The average particle diameter of the microparticles was 352 nm, CV value was 21%, coloring intensity was 2.9 ABS, the proportion of the colored component was 49%, sphericity was 1.2, and the prevalence of coarse particles was 1.4%. An electron micrograph of the resulting colored cellulose microparticles is shown in FIG. 3.

[Preparation of Antibody-Sensitized Colored Cellulose Particles]

60 μl of the 1.0 wt % colored cellulose particles 1 prepared using a known method (average particle diameter: 352 nm, coloring intensity: 2.9 ABS, proportion of colored component: 49%, sphericity: 1.2, prevalence of coarse particles: 1.4%) were placed in a 15 ml centrifuge tube followed by the further addition of 540 μl of Tris buffer (10 mM, pH 7.0) and 60 μl of 0.1% anti-hCG-α mouse antibody (Fitzgerald, 10-C25C) and stirring for 10 seconds with a vortex stirrer. The mixture was placed in a dryer adjusted to 37° C. and allowed to stand undisturbed for 120 minutes. 7.2 ml of a blocking liquid (100 mM boric acid, pH 8.5) containing 1.0 wt % casein (Wako Pure Chemical Industries, Ltd., 030-01505) were added followed by additionally allowing to stand undisturbed for 60 minutes in the dryer at 37° C. Centrifugation at 10000 g was carried out for 15 minutes using a centrifuge (Kubota Corp., 6200) and centrifugal rotor (Kubota Corp., AF-5008C) and the supernatant was removed after the sensitized particles had settled. 7.2 ml of borate buffer (50 mM boric acid, pH 10.0) were added followed by treating for 10 seconds with an ultrasonic disperser (SMT Co., Ltd., UH-50). Centrifugation at 10000 g was carried out for 15 minutes and the supernatant was removed after the sensitized particles had settled. Separate therefrom, the weight of the dispersion of sensitized particles was adjusted to 1.58 g using a buffer obtained by dissolving 1.8 g of sucrose (Wako Pure Chemical Industries Co., Ltd., 196-00015) and 2.4 g of 1.0 wt % casein blocking liquid in 7.2 ml of borate buffer (50 mM boric acid, pH 10.0) to prepare a 0.038 wt % antibody-sensitized colored cellulose dispersion followed by treating for 10 seconds with an ultrasonic disperser.

[Impregnation of Conjugate Pad with Antibody-Sensitized Colored Cellulose Particles and Drying]

A polyethylene conjugate pad (Pall Corp., 6613) was immersed in a large excess of 0.05 wt % TWEEN-20® (Sigma-Aldrich Corp., T2700) followed by drying for 60 minutes at 50° C. after having removed excess liquid. The conjugate pad was then cut to a height of 10 mm and length of 300 mm. 780 μl of the 0.038 wt % antibody-sensitized colored cellulose particle dispersion were uniformly coated thereon using a micropipette followed by drying for 60 minutes at 50° C.

[Pretreatment of Sample Pad]

A cellulose sample pad prepared using a known method (Millipore Corp., C083) was impregnated with a large excess of PBS buffer (66 mM, pH 7.4) containing 2.0 wt % BSA (Sigma-Aldrich Corp., A7906) and 2.0 wt % TWEEN-20@ followed by drying for 60 minutes at 50° C. after removing excess liquid and cutting to a shape having a height of 20 mm and length of 300 mm.

[Preparation of Captured Antibody-Coated Nitrocellulose Membrane]

A nitrocellulose membrane (Millipore Corp., SHF0900425) was cut to a shape having a height of 25 mm and length of 300 mm. A PBS solution (66 mM, pH 7.4) containing 0.1 wt % anti-hCG-β mouse antibody (Medix Biochemica Ab, 6601) was coated to a height of 7 mm at the rate of 0.1 μl/mm using a liquid coating system (Musashi Engineering, Inc., 300DS). PBS solution (66 mM, pH 7.4) containing 0.1 wt % anti-mouse rabbit antibody (Daco Inc., Z0259) was coated onto a portion having a height of 12 mm at the rate of 0.1 μl/mm followed by drying for 30 minutes at 37° C.

[Preparation of Immunochromatographic Diagnostic Kit]

The prepared captured antibody-coated nitrocellulose membrane, absorbent pad (Millipore Corp., C083), conjugate pad containing antibody-sensitized colored cellulose particles and regenerated cellulose continuous long fiber nonwoven fabric sample pad were laminated on a backing card (Adhesives Research Pte. Ltd., AR9020) in the layout shown in FIG. 1 followed by cutting to a width of 5 mm with a cutter to obtain an immunochromatographic diagnostic kit having a width of 5 mm and height of 60 mm.

[Performance Evaluation of Immunochromatographic Diagnostic Kit]

The performance of the resulting immunochromatographic diagnostic kit was evaluated. The results are shown in the following Table 1.

Examples 2-6

With the exception of adjusting the cellulose microparticles to the degrees of polymerization described in the following Table 1, colored particles were produced using the same method as Example 1 and immunochromatographic diagnostic kits were prepared followed by evaluating the performance thereof. The results are shown in the following Table 1.

Examples 7-9

With the exception of dyeing cellulose particles using a reactive dye having a pyrimidine structure (Levafix Rubine CA GR® manufactured by Dystar Group (Example 7), Levafix Navy Blue E-BNA CA GR® manufactured by Dystar Group (Example 8), or Levafix Navy CA GR® manufactured by Dystar Group (Example 9)), colored particles were produced using the same method as Example 1 to prepare immunochromatographic diagnostic kits followed by evaluating the performance thereof. The results are shown in the following Table 1.

Examples 10-13

With the exception of producing colored particles having the diameters described in the following Table 1 by adjusting the production conditions of the cellulose microparticles, immunochromatographic diagnostic kits were prepared using the same method as Example 1 followed by evaluating the performance thereof. The results are shown in the following Table 1.

Examples 14-18

With the exception of producing colored particles having the coloring intensities described in the following Table 1 by adjusting the production conditions of the coloring particles, immunochromatographic diagnostic kits were prepared using the same method as Example 1 followed by evaluating the performance thereof. The results are shown in the following Table 1.

Examples 19-22

With the exception of producing colored particles having the proportions of coarse particles described in the following Table 1 by mixing coloring particles, immunochromatographic diagnostic kits were prepared using the same method as Example 1 followed by evaluating the performance thereof. The results are shown in the following Table 1.

Examples 23, 24

With the exception of producing colored particles having the CV values and proportions of coarse particles described in the following Table 1 by mixing coloring particles, immunochromatographic diagnostic kits were prepared using the same method as Example 1 followed by evaluating the performance thereof. The results are shown in the following Table 1.

Comparative Examples 1, 2

With the exception of producing colored particles having the sphericities described in the following Table 2 by adjusting cellulose microparticles to the degrees of polymerization described in the following Table 2 and adjusting the concentration of tetrahydrofuran in the coagulation liquid, immunochromatographic diagnostic kits were prepared using the same method as Example 1 followed by evaluating the performance thereof. The results are shown in the following Table 2.

Comparative Example 3

With the exception of producing colored particles having the sphericity described in the following Table 2 by adjusting cellulose microparticles to the degree of polymerization described in the following Table 2, an immunochromatographic diagnostic kit was prepared using the same method as Example 1 followed by evaluating the performance thereof. The results are shown in the following Table 2.

Comparative Examples 4-6

With the exception of dyeing while adjusting coloring intensity by adjusting the amount of dye used using the same method as PTL3, immunochromatographic diagnostic kits were prepared using the same method as Example 1 followed by evaluating the performance thereof. The results are shown in the following Table 2.

Comparative Example 7

With the exception of dyeing by adding 12 g of sodium carbonate instead of sodium hydroxide during dyeing, an immunochromatographic diagnostic kit was prepared using the same method as Example 1 followed by evaluating the performance thereof. The results are shown in the following Table 2.

Comparative Examples 8, 9

With the exception of using a reactive dye not having a pyrimidine structure of triazine structure (C.I. Reactive Orange 16 (Example 8) or C.I. Reactive Blue 19 (Example 9)), immunochromatographic diagnostic kits were prepared using the same method as Example 1 followed by evaluating the performance thereof. The results are shown in the following Table 2.

Comparative Examples 10, 11

With the exception of producing colored particles having the average particle diameters shown in the following Table 2 by adjusting the concentration of tetrahydrofuran of the coagulation liquid when producing cellulose particles, immunochromatographic diagnostic kits were prepared using the same method as Example 1 followed by evaluating the performance thereof. The results are shown in the following Table 2.

Comparative Example 12

With the exception of producing colored particles having the coloring intensity described in the following Table 2 by adjusting the production conditions of the coloring particles, an immunochromatographic diagnostic kit was prepared using the same method as Example 1 followed by evaluating the performance thereof. The results are shown in the following Table 2.

Comparative Examples 13-15

With the exception of producing colored particles having the amounts of coarse particles described in the following Table 2 by adjusting the coloring particles of Example 20 and Comparative Example 3 by mixing a prescribed ratio, immunochromatographic diagnostic kits were prepared using the same method as Example 1 followed by evaluating the performance thereof. The results are shown in the following Table 2.

Comparative Examples 16, 17

With the exception of using gold colloid (Comparative Example 16) or latex (Comparative Example 17) as coloring particles, immunochromatographic diagnostic kits were prepared using the same method as Example 1 followed by evaluating the performance thereof. The results are shown in the following Table 2.

TABLE 1

| | | | | | Organic Colored Particles | | | | | | |
|---|---|---|---|---|---|---|---|---|---|---|---|
| Run | Composition | Cellulose Particle Degree of Polymerization | Dyeing Method | Presence of Pyrimidine Structure or Triazine Structure in Dye | Avg. Particle Diameter nm | % CV | Coloring Intensity — | Proportion of Colored Component % | Coarse Particles % | Sphericity (L/D) — | Hydrophilicity — |
| Ex. 1 | Cellulose | 110 | NaOH | Triazine | 352 | 21 | 2.9 | 49 | 1.4 | 1.2 | 12.5 |
| Ex. 2 | Cellulose | 50 | NaOH | Triazine | 356 | 15 | 2.4 | 41 | 0.5 | 2.3 | 10.3 |
| Ex. 2 | Cellulose | 70 | NaOH | Triazine | 354 | 20 | 2.3 | 39 | 0.6 | 2.0 | 9.9 |
| Ex. 3 | Cellulose | 150 | NaOH | Triazine | 348 | 15 | 2.1 | 35 | 0.9 | 1.2 | 9.1 |
| Ex. 4 | Cellulose | 180 | NaOH | Triazine | 368 | 13 | 2.9 | 49 | 0.8 | 1.2 | 12.5 |
| Ex. 5 | Cellulose | 250 | NaOH | Triazine | 330 | 25 | 2.8 | 47 | 2.1 | 1.2 | 18.1 |
| Ex. 6 | Cellulose | 380 | NaOH | Triazine | 322 | 21 | 2.5 | 42 | 4.9 | 1.2 | 19.3 |
| Ex. 7 | Cellulose | 110 | NaOH | Pyrimidine | 380 | 19 | 2.6 | 44 | 1.1 | 1.3 | 6.8 |
| Ex. 8 | Cellulose | 110 | NaOH | Pyrimidine | 321 | 15 | 2.5 | 42 | 1.1 | 1.1 | 12.5 |
| Ex. 9 | Cellulose | 110 | NaOH | Pyrimidine | 333 | 24 | 2.4 | 41 | 1.0 | 1.5 | 7.1 |
| Ex. 10 | Cellulose | 150 | NaOH | Triazine | 120 | 19 | 2.9 | 49 | 0.4 | 1.2 | 12.5 |
| Ex. 11 | Cellulose | 150 | NaOH | Triazine | 290 | 16 | 2.0 | 34 | 0.8 | 1.6 | 8.6 |
| Ex. 12 | Cellulose | 150 | NaOH | Triazine | 450 | 18 | 2.5 | 42 | 1.9 | 1.2 | 10.8 |
| Ex. 13 | Cellulose | 150 | NaOH | Triazine | 600 | 24 | 2.1 | 35 | 4.7 | 1.3 | 10.0 |
| Ex. 14 | Cellulose | 140 | NaOH | Triazine | 295 | 23 | 1.1 | 32 | 1.6 | 1.2 | 29.1 |
| Ex. 15 | Cellulose | 140 | NaOH | Triazine | 305 | 23 | 1.8 | 37 | 1.6 | 1.4 | 21.5 |
| Ex. 16 | Cellulose | 140 | NaOH | Triazine | 311 | 23 | 2.4 | 43 | 1.0 | 1.4 | 5.9 |
| Ex. 17 | Cellulose | 140 | NaOH | Triazine | 421 | 27 | 3.8 | 59 | 1.2 | 1.2 | 2.8 |
| Ex. 18 | Cellulose | 140 | NaOH | Triazine | 510 | 28 | 6.0 | 81 | 4.7 | 1.3 | 1.5 |

TABLE 1-continued

| Ex. 19 | Cellulose | 100 | NaOH | Triazine | 315 | 26 | 2.7 | 46 | 0.2 | 1.1 | 11.6 |
| Ex. 20 | Cellulose | 120 | NaOH | Triazine | 376 | 18 | 2.5 | 42 | 0.8 | 1.1 | 10.8 |
| Ex. 21 | Cellulose | 110 | NaOH | Triazine | 366 | 11 | 2.6 | 44 | 3.9 | 1.1 | 11.2 |
| Ex. 22 | Cellulose | 150 | NaOH | Triazine | 323 | 10 | 2.5 | 42 | 4.7 | 1.1 | 10.8 |
| Ex. 23 | Cellulose | 180 | NaOH | Triazine | 375 | 38 | 2.3 | 39 | 0.5 | 1.1 | 9.9 |
| Ex. 24 | Cellulose | 190 | NaOH | Triazine | 368 | 40 | 2.1 | 35 | 1.2 | 1.3 | 8.5 |

| | Organic Colored Particles | Immunochromatography Results | | | | |
| | Relative element | Diagnosis Time | | TL Intensity | | | | |
| Run | concentration of elemental F atomic % | Avg. Time Second | Reproducibility % CV | Avg. intensity mABS | Reproducibility % CV | Background mABS | False Positivity | Detection Limit mIU |
|---|---|---|---|---|---|---|---|---|
| Ex. 1 | 1.2 | 35 | 7.2 | 405 | 3.1 | 2 | None | 0.10 |
| Ex. 2 | 0.9 | 38 | 10.8 | 405 | 6.8 | 5 | None | 0.10 |
| Ex. 2 | 0.9 | 35 | 10.5 | 410 | 6.5 | 5 | None | 0.10 |
| Ex. 3 | 0.7 | 31 | 8.4 | 410 | 3.5 | 2 | None | 0.10 |
| Ex. 4 | 1.1 | 35 | 8.5 | 415 | 3.4 | 3 | None | 0.10 |
| Ex. 5 | 0.9 | 36 | 7.1 | 415 | 3.8 | 2 | None | 0.10 |
| Ex. 6 | 0.8 | 35 | 10.5 | 480 | 8.5 | 5 | None | 0.05 |
| Ex. 7 | 0.9 | 38 | 7.3 | 405 | 3.6 | 2 | None | 0.10 |
| Ex. 8 | 0.9 | 32 | 7.1 | 395 | 3.4 | 1 | None | 0.10 |
| Ex. 9 | 0.8 | 35 | 7.8 | 400 | 3.0 | 2 | None | 0.10 |
| Ex. 10 | 1.0 | 32 | 7.5 | 315 | 3.5 | 3 | None | 0.20 |
| Ex. 11 | 0.7 | 32 | 7.5 | 390 | 3.5 | 1 | None | 0.10 |
| Ex. 12 | 0.7 | 31 | 7.6 | 450 | 3.6 | 2 | None | 0.05 |
| Ex. 13 | 0.7 | 35 | 7.4 | 480 | 3.4 | 5 | None | 0.05 |
| Ex. 14 | 0.1 | 35 | 15.3 | 330 | 7.0 | 1 | None | 0.20 |
| Ex. 15 | 0.2 | 36 | 11.2 | 350 | 4.9 | 3 | None | 0.20 |
| Ex. 16 | 0.9 | 36 | 5.5 | 450 | 3.5 | 5 | None | 0.10 |
| Ex. 17 | 4.1 | 35 | 5.1 | 505 | 3.6 | 5 | None | 0.05 |
| Ex. 18 | 6.8 | 29 | 5.2 | 495 | 3.5 | 5 | None | 0.05 |
| Ex. 19 | 0.9 | 32 | 5.5 | 330 | 3.5 | 1 | None | 0.20 |
| Ex. 20 | 0.7 | 39 | 7.3 | 410 | 3.5 | 4 | None | 0.10 |
| Ex. 21 | 0.7 | 35 | 6.8 | 460 | 3.4 | 5 | None | 0.05 |
| Ex. 22 | 0.7 | 32 | 6.9 | 480 | 3.8 | 5 | None | 0.05 |
| Ex. 23 | 0.8 | 36 | 7.5 | 405 | 7.1 | 2 | None | 0.10 |
| Ex. 24 | 0.7 | 32 | 7.1 | 395 | 6.9 | 2 | None | 0.10 |

TABLE 2

| | Organic Colored Particles | | | | | | | | |
| Run | Cellulose Composition | Particle Degree of Polymerization | Dyeing Method | Presence of Pyrimidine Structure or Triazine Structure in Dye | Avg. Particle Diameter nm | % CV | Coloring Intensity — | Proportion of Colored Component % | Coarse Particles % | Sphericity (L/D) — | Hydro-philicity — |
|---|---|---|---|---|---|---|---|---|---|---|---|
| Comp. Ex. 1 | Cellulose | 20 | NaOH | Triazine | 335 | 29 | 2.5 | 42 | 4.6 | 3.5 | 10.8 |
| Comp. Ex. 2 | Cellulose | 20 | NaOH | Triazine | 325 | 15 | 2.5 | 42 | 6.2 | 5.0 | 10.8 |
| Comp. Ex. 3 | Cellulose | 560 | NaOH | Triazine | 421 | 25 | 2.6 | 44 | 10.1 | 1.2 | 11.2 |
| Comp. Ex. 4 | Cellulose | 110 | $Na_2CO_3$ | Triazine | 330 | 22 | 1.1 | 29 | 5.9 | 2.9 | 57.1 |
| Comp. Ex. 5 | Cellulose | 110 | $Na_2CO_3$ | Triazine | 336 | 26 | 2.4 | 43 | 7.3 | 2.7 | 54.3 |
| Comp. Ex. 6 | Cellulose | 110 | $Na_2CO_3$ | Triazine | 354 | 23 | 4.9 | 61 | 8.1 | 2.2 | 50.1 |
| Comp. Ex. 7 | Cellulose | 110 | $Na_2CO_3$ | Triazine | 396 | 22 | 2.7 | 45 | 8.8 | 2.7 | 53.0 |
| Comp. Ex. 8 | Cellulose | 110 | NaOH | Absent | 345 | 15 | 0.6 | 40 | 3.8 | 1.9 | 82.3 |
| Comp. Ex. 9 | Cellulose | 110 | NaOH | Absent | 356 | 16 | 0.8 | 59 | 2.1 | 1.5 | 75.4 |
| Comp. Ex. 10 | Cellulose | 110 | NaOH | Triazine | 70 | 25 | 2.4 | 41 | 0.6 | 1.2 | 10.3 |
| Comp. Ex. 11 | Cellulose | 110 | NaOH | Triazine | 720 | 26 | 2.5 | 42 | 16.3 | 1.3 | 10.8 |
| Comp. Ex. 12 | Cellulose | 110 | NaOH | Triazine | 366 | 22 | 0.7 | 8 | 1.2 | 1.5 | 38.8 |

TABLE 2-continued

| Run | | | | | | | | | |
|---|---|---|---|---|---|---|---|---|---|
| Comp. Ex. 13 | Cellulose | — | NaOH | Triazine | 386 | 25 | 2.3 | 39 | 7.5 | 1.5 | 9.9 |
| Comp. Ex. 14 | Cellulose | — | NaOH | Triazine | 369 | 20 | 2.5 | 42 | 9.1 | 1.5 | 10.8 |
| Comp. Ex. 15 | Cellulose | — | NaOH | Triazine | 365 | 21 | 2.5 | 42 | 8.4 | 1.4 | 10.8 |
| Comp. Ex. 16 | Gold Colloid | — | — | — | 50 | 18 | 2.4 | — | 0.1 | 1.5 | 1.5 |
| Comp. Ex. 17 | Latex | — | — | — | 470 | 15 | 0.5 | — | 0.5 | 1.2 | 1.7 |

| | Organic Colored Particles | Immunochromatography Results | | | | | |
|---|---|---|---|---|---|---|---|
| | Relative element | Diagnosis Time | | TL Intensity | | | |
| Run | concentration of elemental F atomic % | Avg. Time Second | Reproducibility % CV | Avg. intensity mABS | Reproducibility % CV | Background mABS | False Positivity | Detection Limit mIU |
| Comp. Ex. 1 | 0.8 | 45 | 29.0 | 375 | 11.5 | 11 | Yes | — |
| Comp. Ex. 2 | 1.2 | 41 | 29.5 | 390 | 13.5 | 10 | Yes | — |
| Comp. Ex. 3 | 0.5 | 35 | 26.0 | 480 | 5.0 | — | — | — |
| Comp. Ex. 4 | N.D. | 36 | 27.1 | 320 | 16.8 | 15 | — | — |
| Comp. Ex. 5 | N.D. | 32 | 22.5 | 410 | 12.5 | 8 | None | 0.10 |
| Comp. Ex. 6 | N.D. | 32 | 23.0 | 385 | 12.6 | 9 | None | 0.10 |
| Comp. Ex. 7 | N.D. | 36 | 20.0 | 375 | 16.5 | 15 | — | — |
| Comp. Ex. 8 | N.D. | 85 | 12.5 | 290 | 19.5 | 2 | None | 4.00 |
| Comp. Ex. 9 | N.D. | 65 | 15.0 | 315 | 21.0 | 3 | None | 2.00 |
| Comp. Ex. 10 | 0.9 | 36 | 5.4 | 245 | 2.1 | 1 | None | 1.00 |
| Comp. Ex. 11 | 0.8 | 20 | 2.6 | 520 | 8.5 | 11 | Yes | — |
| Comp. Ex. 12 | 0.2 | 35 | 5.3 | 280 | 15.3 | 3 | None | 1.00 |
| Comp. Ex. 13 | 0.8 | 31 | 21.3 | 475 | 5.6 | 15 | — | — |
| Comp. Ex. 14 | 0.8 | 32 | 23.5 | 465 | 5.5 | 13 | — | — |
| Comp. Ex. 15 | 0.9 | 36 | 21.0 | 480 | 3.5 | 14 | — | — |
| Comp. Ex. 16 | N.D. | 110 | 7.5 | 200 | 18.0 | 2 | None | 1.00 |
| Comp. Ex. 17 | N.D. | 130 | 7.8 | 150 | 17.0 | 2 | None | 3.00 |

INDUSTRIAL APPLICABILITY

An immunochromatographic diagnostic kit using the organic colored microparticles according to the present invention has favorable background and test result reproducibility and can be preferably used as a diagnostic reagent having adequate detection sensitivity.

REFERENCE SIGNS LIST (a) Sample pad
(b) Conjugate pad containing antibody-sensitized coloring particles
(c) Detection portion A (TL)
(d) Detection portion B (control line)
(e) Chromatographic medium
(f) Absorbent pad
(g) Mount

The invention claimed is:

1. A dispersion of colored cellulose microparticles comprising:
    (i) organic colored cellulose microparticles in which an average microparticle diameter is 100-650 nm,
    (ii) a coloring intensity is 1.0-10.0,
    (iii) a number of the organic colored cellulose microparticles having a particle diameter of 700 nm to 12000 nm per a number of the organic colored cellulose microparticles having a particle diameter from 400 nm to 12000 nm in the dispersion is 0.2 to 5%,
    (iv) a sphericity of the organic colored cellulose particles as represented by major axis (L)/minor axis (D) is 1.0-2.5,
    (v) the organic colored cellulose microparticles include a dye having a pyrimidine structure or triazine structure and contain elemental fluorine (F), and
    (vi) a relative concentration of the elemental fluorine (F) on a surface of the organic colored cellulose microparticle as determined by x-ray photoelectron spectroscopy (XPS) is 0.1 atomic % to 6.8 atomic %.

2. The dispersion of colored cellulose microparticles according to claim 1, wherein the relative element concentration of the elemental fluorine (F) on the surface of the organic colored cellulose microparticle as determined by the x-ray photoelectron spectroscopy (XPS) is 0.2 atomic % to 6.8 atomic %.

3. The dispersion of colored cellulose microparticles according to claim 1, wherein the relative element concentration of the elemental fluorine (F) on the surface of the organic colored cellulose microparticle surface as determined by the x-ray photoelectron spectroscopy (XPS) is 0.3 atomic % to 6.8 atomic %.

4. The dispersion of colored cellulose microparticles according to claim 1, wherein hydrophilicity of the organic colored cellulose microparticles is 1.0 to 30.0.

5. The dispersion of colored cellulose microparticles according to claim 1, wherein hydrophilicity of the organic colored cellulose microparticles is 1.5 to 27.0.

6. The dispersion of colored cellulose microparticles according to claim 1, wherein hydrophilicity of the organic colored cellulose microparticles is 2.0 to 25.0.

7. A polyethylene conjugate pad comprising the dispersion of colored cellulose microparticles of claim 1, wherein the dispersion of colored cellulose microparticles is coated on the polyethylene conjugate pad.

8. A diagnostic reagent kit containing the dispersion of colored cellulose microparticles according to claim 1.

9. The diagnostic reagent kit according to claim 8, wherein the diagnostic reagent kit is an immunochromatographic kit.

10. A diagnostic reagent kit containing the polyethylene conjugate pad according to claim 7.

11. The diagnostic reagent kit according to claim 10, wherein the diagnostic reagent kit is an immunochromatographic kit.

* * * * *